US011752135B2

(12) United States Patent
Schuetz et al.

(10) Patent No.: US 11,752,135 B2
(45) Date of Patent: *Sep. 12, 2023

(54) LIQUID PHARMACEUTICAL FORMULATION

(71) Applicant: Project Pharmaceutics GmbH, Martinsried (DE)

(72) Inventors: Andreas Schuetz, Martinsried (DE); Klaus Hellerbrand, Martinsried (DE)

(73) Assignee: PROJECT PHARMACEUTICS GMBH, Martinsried (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/042,795

(22) PCT Filed: Mar. 29, 2019

(86) PCT No.: PCT/EP2019/057984
§ 371 (c)(1),
(2) Date: Sep. 28, 2020

(87) PCT Pub. No.: WO2019/185859
PCT Pub. Date: Oct. 3, 2019

(65) Prior Publication Data
US 2021/0023059 A1   Jan. 28, 2021

(30) Foreign Application Priority Data
Mar. 29, 2018 (LU) ........................................ 100750

(51) Int. Cl.
| | | |
|---|---|---|
| *A61K 31/4184* | (2006.01) | |
| *A61K 31/192* | (2006.01) | |
| *A61K 47/02* | (2006.01) | |
| *A61K 47/34* | (2017.01) | |
| *A61K 31/198* | (2006.01) | |
| *A61K 31/216* | (2006.01) | |

(52) U.S. Cl.
CPC ........ *A61K 31/4184* (2013.01); *A61K 31/192* (2013.01); *A61K 31/198* (2013.01); *A61K 31/216* (2013.01); *A61K 47/02* (2013.01); *A61K 47/34* (2013.01)

(58) Field of Classification Search
None
See application file for complete search history.

(56) References Cited

U.S. PATENT DOCUMENTS

| | | | | |
|---|---|---|---|---|
| 2002/0107173 A1* | 8/2002 | Friedhoff | ........... | G01N 33/6896 514/460 |
| 2011/0184036 A1* | 7/2011 | Palepu | ................. | A61K 47/186 514/394 |
| 2014/0005148 A1 | 1/2014 | Neelakantan et al. | | |
| 2015/0258069 A1* | 9/2015 | Voudouris | ............... | A61P 35/02 514/394 |

FOREIGN PATENT DOCUMENTS

| | | |
|---|---|---|
| CA | 1162479 A | 2/1984 |
| CN | 101856325 A | 10/2010 |
| DE | 0159289 Z | 3/1983 |
| JP | S63239237 A2 | 10/1988 |
| JP | H11292767 A2 | 10/1999 |
| LU | 100750 A | 3/2018 |
| WO | 95033487 A1 | 12/1995 |
| WO | 2010036702 A1 | 4/2010 |
| WO | 2011094565 A1 | 8/2011 |
| WO | 2013112762 A1 | 8/2013 |
| WO | 2015138199 A1 | 9/2015 |
| WO | 2017002030 A1 | 1/2017 |
| WO | 2019185859 A1 | 10/2019 |

OTHER PUBLICATIONS

Sigma Aldrich Website, Poly(ethylene glycol) entry [online]. Mar. 22, 2022 [retrieved on Mar. 22, 2022]. Retrieved from the internet: <https://www.sigmaaldrich.com/US/en/product/sial/81170>. (Year: 2022).*
PubChem Website, Propylene Glycol enter [online]. Mar. 22, 2022 [retrieved on Mar. 22, 2022]. Retrieved from the internet: <https://pubchem.ncbi.nlm.nih.gov/compound/Propylene-glycol>.(Year: 2022).*
Eagle Pharmaceuticals, Inc., BELRAPZO Highlights of Prescribing Information, Revised Aug. 2018, 23 pages.
Johnson et al., Toward Hypoxia-Selective DNA-Alkylating Agents Built by Grafting Nitrogen Mustards onto the Bioreductively Activated, HypoxiaSelective DNA-Oxidizing Agent 3-Amino-1,2,4-benzotriazine 1,4-Dioxide (Tirapazaminie). J Org Chem. Aug. 15, 2014;79(16):7520-31.
Pearson, Acids and Bases, Sciences. Jan. 14, 1966;151(3707):172-177. Pearson, Hard and Soft Acids and Bases, HSAB, Part I. J Chem Ed. 1968;45(9):581-587.
Sheskey et al., "Calcium Chloride" found in: Handbook of Pharmaceutical Excipients, 8th Edition (2017), pp. 141-143.
Wikipedia, "Cisplatin". original file name: Cisplatin—Wikipedia—Dec. 13, 2017—Wayback Machine.pdf. Accessed online at: https://en.wikipedia.org/wiki/Cisplatin (dowloaded at https://web.archive.org/web/20171213225742/https://en.wikipedia.org/wiki/Cisplatin).
Notice of Opposition filed in European Patent No. 3773498 dated Mar. 22, 2023 (28 pages).

* cited by examiner

*Primary Examiner* — Katherine Peebles

(74) *Attorney, Agent, or Firm* — ACUITY LAW GROUP, PC; Michael A. Whittaker

(57) ABSTRACT

The present invention relates to a liquid pharmaceutical formulation, which is stable at room temperature, being essentially free of water, comprising a) at least one easily degradable active pharmaceutical ingredient, b) at least one pharmaceutically acceptable organic solvent and c) at least one pharmaceutically acceptable alkaline earth metal salt and its use in medicine.

16 Claims, 19 Drawing Sheets

LIQUID PHARMACEUTICAL FORMULATION

PRIORITY CLAIM

This application claims priority to International Application No. PCT/EP2019/057984, filed Mar. 29, 2019, which claims priority to Luxembourg Application No. 100750, filed Mar. 29, 2018, wherein the contents of said applications are incorporated herein by reference in their entireties.

TECHNICAL FIELD OF THE INVENTION

The present invention relates to a liquid pharmaceutical formulation, being essentially free of water, comprising a) at least one easily degradable active pharmaceutical ingredient b) at least one pharmaceutically acceptable organic solvent and c) at least one pharmaceutically acceptable alkaline earth metal salt and its use in medicine.

BACKGROUND ART

Certain pharmaceutical ingredients are degradable e.g. due to hydrolysis. An exemplary group of degradable pharmaceutical ingredients are alkylating agents which are used for the treatment of various cancers. One substance of this group, for example is Bendamustine. Bendamustine comprises an alkylating —$N((CH_2)_2Cl)_2$ group, which undergoes rapid hydrolysis, by substitution of the chloride groups, to the corresponding mono- and di-hydroxy compounds. The hydrolysis of Bendamustine in water takes place in hours, therefore a solution of Bendamustine is not suitable for long term storage. Bendamustine is commercially available as powder in lyophilized form as Treanda™. While the lyophilized form exhibits good chemical stability, with implications of chemical stability. Thus, efforts have been made to stabilize Bendamustine in liquid pharmaceutical formulations, which may be stored for longer time.

In this respect, WO2011/094565 discloses a formulation for long term storage including bendamustine or a pharmaceutically acceptable salt thereof; a pharmaceutically acceptable fluid including polyethylene glycol PEG, propylene glycol (PG) and a stabilizing amount of an antioxidant such as thioglycerol. Another formulation includes bendamustine or a pharmaceutically acceptable salt thereof; a pharmaceutically acceptable fluid including polyethylene glycol PEG), propylene glycol (PG), ethanol, benzyl alcohol and glycofurol and a chloride salt such as sodium chloride, choline chloride, and hydrochloride salts of amino acids.

WO 2013/112762 A1 deals with aqueous Bendamustine formulations with improved stability. These comprise a mixture of a non-aqueous solvent system and an aqueous chloride-containing water phase. The non-aqueous solvent may comprise propylene glycol or polyethylene glycol and optionally antioxidants and preservatives such as thioglycerol.

The aim of the present invention is therefore to provide an optimized pharmaceutical formulation for stabilizing easily degradable active pharmaceutical ingredients.

SUMMARY OF THE INVENTION

The Invention relates to a liquid pharmaceutical formulation, being essentially free of water, comprising
a) at least one easily degradable active pharmaceutical ingredient,
b) at least one pharmaceutically acceptable organic solvent and
c) at least one pharmaceutically acceptable alkaline earth metal salt.

Further, the invention is directed to the pharmaceutical formulation for use in medicine as well as to the pharmaceutical formulation for use in the treatment of cancer.

It has been shown that the inventive pharmaceutical formulation is suitable to stabilize easy degradable active pharmaceutical ingredients in comparison to samples which did not comprise at least one pharmaceutically acceptable alkaline earth metal salt. An embodiment wherein the alkaline earth metal salt is $CaCl_2$ proved to be particularly effective for stabilizing easy degradable active pharmaceutical ingredients. Further, the inventive pharmaceutical formulations reduce or prevent color change indicating degradation during storage, in particular in comparison with other pharmaceutical formulations for the same purpose of stabilizing degradable active pharmaceutical ingredients, known in the art. Unlike organic preservatives and antioxidants the addition of alkaline earth metal salts from calcium or magnesia in the amounts described herein are regarded as physiologically safe and do not require any verification. For example, in contrast to the formulation as disclosed in WO2011/094565, the pharmaceutical formulation of the present invention does not require the presence of toxic thioglycerol as antioxidant.

DETAILED DESCRIPTION OF THE INVENTION

Figure 1:
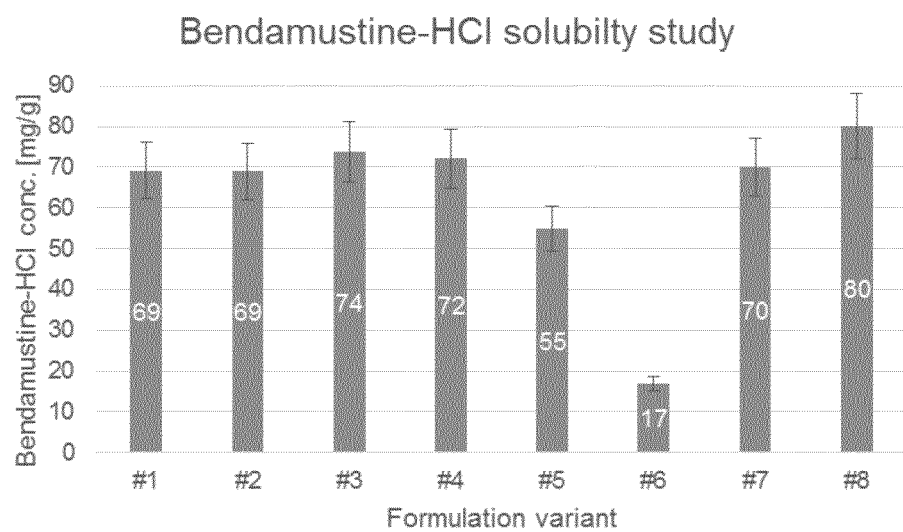
FIG. 1 depicts the results of the Bendamustine-HCl solubility study according to example 2. Target concentration was 80 mg/g after storage over-night at 2-8° C. and subsequent centrifugation. Analysis was performed by RP-HPLC.
Figure 2:
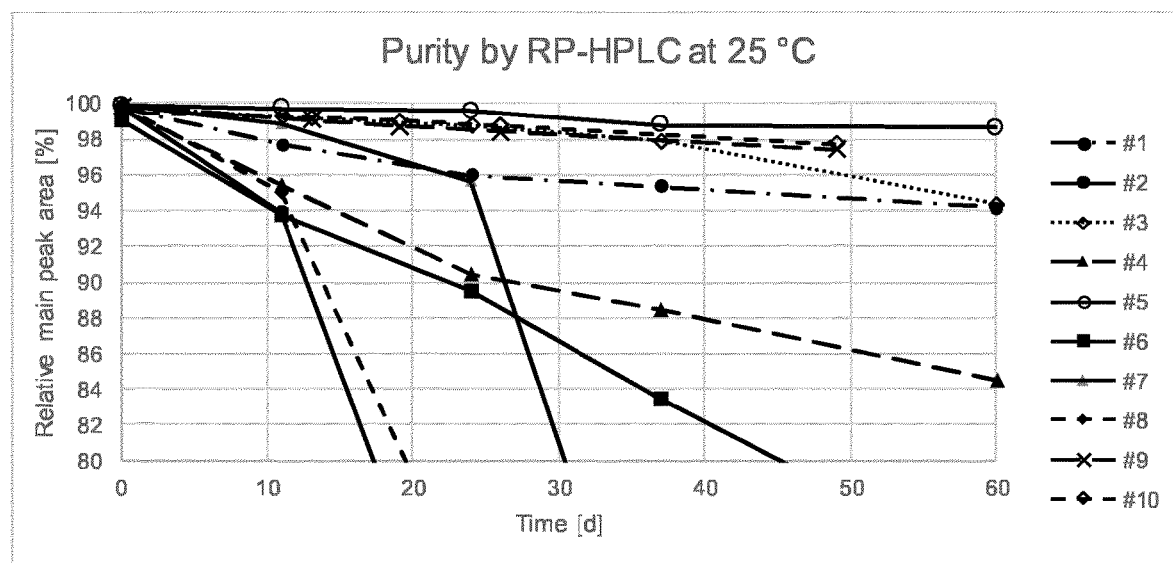
FIG. 2 depicts purity at 25° C. of Bendamustine-HCl in the formulation variants determined by relative main peak evaluation in RP-HPLC chromatograms.
Figure 3:
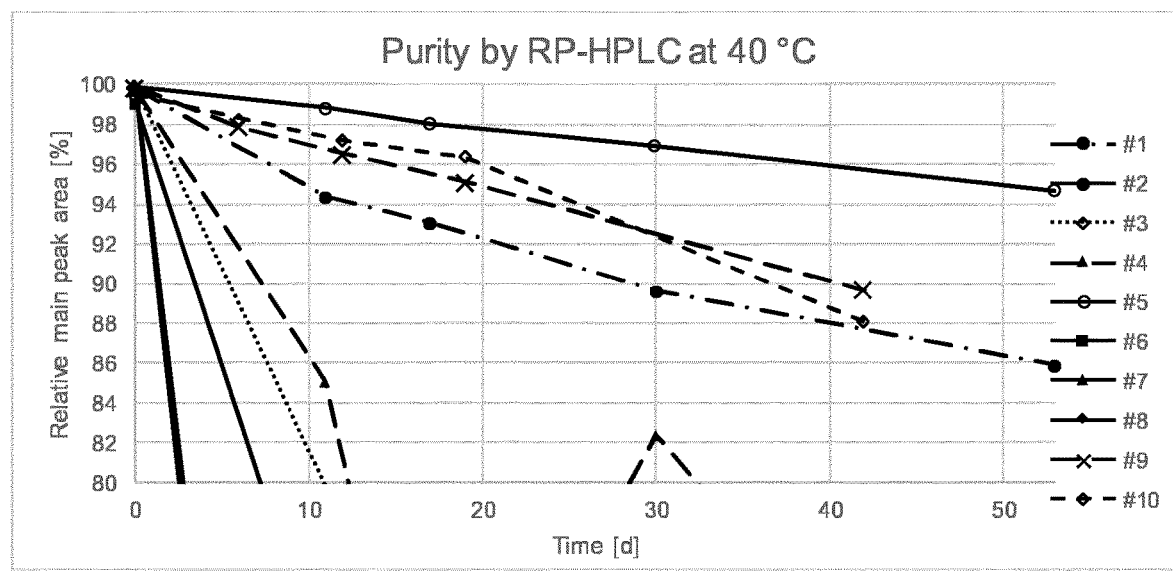
FIG. 3 depicts Purity at 40° C. of Bendamustine-HCl in the formulation variants determined by relative main peak evaluation in RP-HPLC chromatograms.
Figure 4:
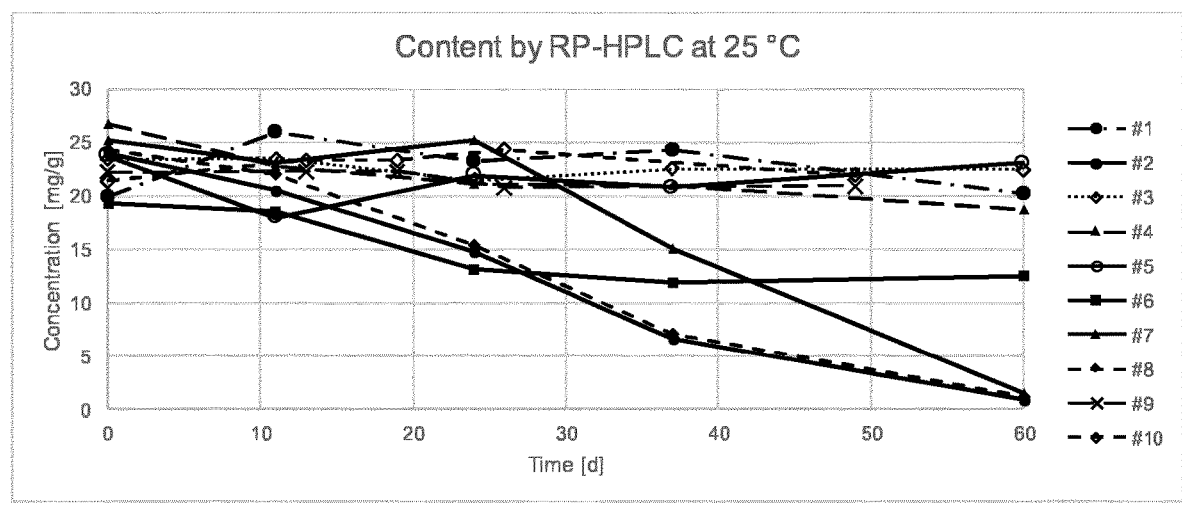
FIG. 4 depicts content at 25° C. of Bendamustine-HCl in the formulation variants determined by relative main peak evaluation in RP-HPLC chromatograms.
Figure 5:
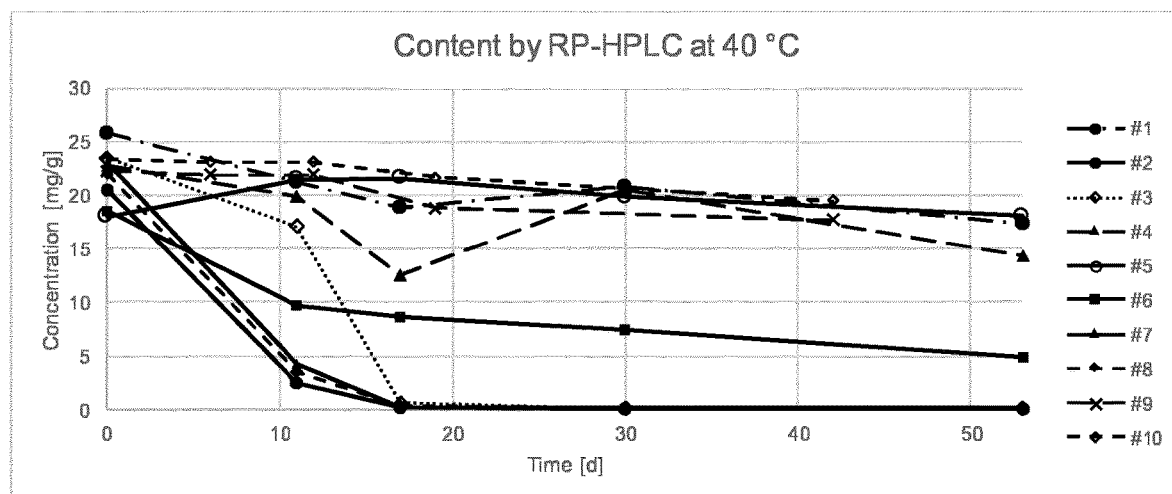
FIG. 5 depicts Purity at 40° C. of Bendamustine-HCl in the formulation variants determined by relative main peak evaluation in RP-HPLC chromatograms.

The solution of the present invention is described in the following, exemplified in the appended examples, illustrated in the Figures and reflected in the claims.

The present invention provides a liquid pharmaceutical formulation, being essentially free of water, comprising
a) at least one aromatic nitrogen mustard active pharmaceutical ingredient,
b) at least one pharmaceutically acceptable organic solvent and
c) at least one pharmaceutically acceptable alkaline earth metal salt.

In the context of the present invention, "essentially free of water" means a water content below 5% (w/w), preferably below 2% (w/w), more preferably below 1% (w/w), most preferably below 0.5% (w/w).

The at least one easily degradable active pharmaceutically ingredient may be any pharmaceutically active ingredient known to the person skilled in the art, which decomposes, is chemically transformed and/or loses its pharmaceutical activity and/or forms detrimental side products due to its degradation during storage in dissolved form. The easily degradable active pharmaceutically ingredient may be used in form of its pharmaceutically acceptable salt, wherein the anion may be inorganic or organic. For example in form of its hydrochloride. In the context of the present invention, the term "degradable active pharmaceutically ingredient" refers to the neutral form and/or the corresponding pharmaceutically and/or pharmaceutically acceptable salt thereof. In the context of the invention, the term "pharmaceutically acceptable" means that the respective substance fulfills at least the necessary legal qualitative requirements for its administration to humans or animals as part of a medical or non-medical treatment.

Preferably, the degradable pharmaceutically active ingredient is at least sensitive to hydrolysis, for example caused by moisture, and/or the degradable pharmaceutically active ingredient is at least sensitive to oxidation, for example caused by oxygen or free radicals, more preferably the degradable pharmaceutically active ingredient is at least sensitive to hydrolysis.

Hydrolysis in the context of the invention means cleavage of one or more bonds by addition of at least one water or alcohol (HO—R) molecule or replacement of a functional group by a hydroxyl group originating from the water molecule. The hydrolysis may include formation of small molecules formed of protons originating from the water or alcohol molecule attached and the group which has been released is for example HCl or HBr.

Degradation of nitrogen mustards (ternary 2,2'-dichloro-alkylamines) is supposed to take place via the formation of a reactive three-member cyclic intermediate towards mono and dihydroxyl products (e.g. hydrolysis or alcoholysis). To start this reaction a free election pair at the nitrogen atom has to be accessible. The presence of positively charged calcium (or other alkaline earth metal) ions reduces the accessibility of the partial negatively charged election pair at the nitrogen atom by charge interactions between the calcium ion and the free electron pair. By masking the said electron pair at the nitrogen atom with calcium ions the cyclization reaction is slowed down or completely blocked resulting in a demonstrable stabilizing effect on nitrogen-mustard compounds:

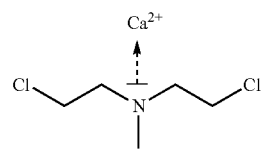

The stabilizing effect is depending on the capability of the alkaline earth metal ion to undergo charge interactions to the election pair at the nitrogen atom. Thus, the degree of dissociation and solvation of the alkaline earth metal salt within the organic solvent and the cation itself (calcium, magnesium or others) as well as the counterion (chloride, bromide, acetate, etc.) have an influence on the extent of stabilization: e.g. $CaBr_2$ shows less effective stabilization compared to $CaCl_2$, caused by the higher atomic radius of bromide compared to chloride. The stabilizing effect of chloride itself without an alkaline earth metal cation (e.g. choline chloride: (2-hydroxyethyl)-trimethylammonium) is shown to be negligible.

More preferably the degradable pharmaceutically active ingredient is an alkylating agent, such as a pharmaceutically active ingredient which is capable of transferring alkyl groups to DNA.

Even more preferred, the degradable active pharmaceutical ingredient comprises at least one group according to formula (I)

wherein in formula (I)
X is Cl or Br, preferably Cl
$R_1$ is H, —$CH_2CH_2X$ or —NO, preferably H or —$CH_2CH_2X$.

Wherein in formula (I) the central nitrogen atom is not substituted by a methyl group, rather the corresponding bond represents the bond to the rest of the overall molecule of the degradable active pharmaceutical ingredient.

Particularly preferred, the degradable active pharmaceutical ingredient is a compound according to formula (II)

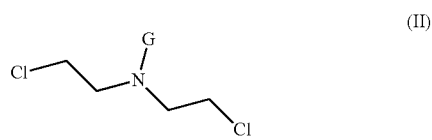

wherein

G is Ar or HetAr

Ar or HetAr is optionally substituted with 1 to 5, preferably 1 to 4, more preferably 1 to 3, particularly preferred 1 to 2, most preferably 1 substituent.

The term "Ar" refers to an aromatic cyclic hydrocarbon. Preferably, the aryl group contains 5 to 7 carbon atoms which can be arranged in one ring (e.g., phenyl) or two or more condensed rings (e.g., naphthyl). Exemplary aryl groups include cyclopropenylium, cyclopentadienyl, phenyl, indenyl, naphthyl, azulenyl, fluorenyl, anthryl, and phenanthryl. Preferably, "aryl" refers to a monocyclic ring containing 6 carbon. A preferred example is phenyl.

The term "HetAr" means an aryl group as defined above in which one or more carbon atoms in the aryl group are replaced by heteroatoms of O, S, or N. Preferably, heteroaryl refers to a five or six-membered aromatic monocyclic ring wherein 1, 2, or 3 carbon atoms are replaced by the same or different heteroatoms of O, N, or S. Alternatively, it means an aromatic bicyclic or tricyclic ring system wherein 1, 2, 3, 4, or 5 carbon atoms are replaced with the same or different heteroatoms of O, N, or S. Preferably, in each ring of the heteroaryl group the maximum number of O atoms is 1, the maximum number of S atoms is 1, and the maximum total number of O and S atoms is 2. Exemplary heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), tetrazolyl, thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), benzofuranyl (1- and 2-), indolyl, isoindolyl, benzothienyl (1- and 2-), 1H-indazolyl, benzimidazolyl, benzoxazolyl, indoxazinyl, benzisoxazolyl, benzothiazolyl, benzisothiazolyl, benzotriazolyl, quinolinyl, isoquinolinyl, benzodiazinyl, quinoxalinyl, quinazolinyl, benzotriazinyl (1,2,3- and 1,2,4-benzotriazinyl), pyridazinyl, phenoxazinyl, thiazolopyridinyl, pyrrolothiazolyl, phenothiazinyl, isobenzofuranyl, chromenyl, xanthenyl, phenoxathiinyl, pyrrolizinyl, indolizinyl, indazolyl, purinyl, quinolizinyl, phthalazinyl, naphthyridinyl (1,5-, 1,6-, 1,7-, 1,8-, and 2,6-), cinnolinyl, pteridinyl, carbazolyl, phenanthridinyl, acridinyl, perimidinyl, phenanthrolinyl (1,7-, 1,8-, 1,10-, 3,8-, and 4,7-), phenazinyl, oxazolopyridinyl, isoxazolopyridinyl, pyrrolooxazolyl, and pyrrolopyrrolyl. Exemplary 5- or 6-membered heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), and pyridazinyl.

Most preferably, the at least one easily degradable active pharmaceutical ingredient is selected from the group consisting of Uramustine, Bendamustine, Melphalan, Melflufen, Chlorambucil, preferably Melphalan, Melflufen, Chlorambucil, Bendamustine, more preferably Bendamustine.

Preferably, the concentration of the at least one degradable active pharmaceutical ingredient in the formulation is 1 to 200 mg/g, more preferably 5 to 150 mg/g, even more preferably 10 to 100 mg/g, most preferably 20 to 40 mg/g based on the overall weight of the formulation.

The at least one pharmaceutically acceptable organic solvent may be any organic solvent which is suitable for physiological use.

Preferably the at least one organic solvent is a pharmaceutically acceptable polyol. More preferably the at least one pharmaceutically acceptable organic solvent is propylene glycol, 1,3-butanediol, polyethylene glycol, such as PEG 400 and/or PEG 300, preferably PEG 400 and/or propylene glycol.

In a further embodiment, the at least one pharmaceutically acceptable organic solvent is a mixture of 5 to 20% Propyleneglycol and 80 to 95% polyethylene glycol (w/w), preferably 10% Propyleneglycol and 90% PEG 400 (w/w).

The at least one pharmaceutically acceptable alkaline earth metal salt may be any pharmaceutically acceptable alkaline earth metal known to the person skilled in the art. In the context of the present invention, "alkaline earth metal salt" means any ionic compound, including coordination complexes and chelate complexes of an alkaline earth metal.

Preferably the at least one earth metal salt is a calcium or a magnesium salt. More preferably a calcium salt. Preferably the anion of the at least one alkaline earth metal salt is gluconate, chloride, bromide, acetate, orotate or lactate more preferably chloride, acetate or lactate, most preferably chloride.

Most preferably the at least one pharmaceutically acceptable alkaline earth metal salt is calcium chloride or magnesium chloride, particularly preferred calcium chloride.

The at least one pharmaceutically acceptable alkaline earth metal salt is preferably present in a concentration of 0.1 to 3 mol/L, more preferably 0.1 to 1.5 mol/L, even more preferred 0.3 to 1.5 mol/L, particular preferred 0.7 to 1.1 mol/L, more particular preferred 0.1 to 1.0 mol/L, most particular preferred 0.8 to 1.0 mol/L, especially preferred 0.1 to 0.5 mol/L based on the overall volume of the liquid formulation.

The at least one pharmaceutically acceptable alkaline earth metal salt in the said concentrations is preferably completely dissolved in the pharmaceutically acceptable organic solvent resulting in a clear pharmaceutical solution.

The liquid pharmaceutical formulation may comprise further additional ingredients known to the person skilled in the art. These may comprise for example buffers, detergents, preservatives and others.

The liquid pharmaceutical formulation may be applied without further dilution or with prior dilution. The pharmaceutical formulation may be diluted with water for injection purposes, saline or buffer solution before administration. Preferably, the pharmaceutical formulation is diluted with water for injection purposes, saline or buffer solution, not longer than 8 hours, preferably not longer than 4 hours and most preferably not longer than 2 hour before administration.

The liquid pharmaceutical formulation may be administered in any suitable manner known to the person skilled in the art. Preferably, the liquid pharmaceutical formulation is administered parenterally, more preferably as injection, most preferably as intravenous infusion or intravenous bolus injection.

In one embodiment, the liquid pharmaceutical formulation, preferably being essentially free of water comprises
  a) 1 to 200 mg/g, preferably 5 to 150 mg/g, more preferably 10 to 100 mg/g, most preferably 20 to 40 mg/g based on the overall weight of the formulation. of the at least one easily degradable active pharmaceutical ingredient,
  b) at least one pharmaceutically acceptable organic solvent and
  c) the at least one pharmaceutically acceptable alkaline earth metal salt is preferably present in a concentration of 0.1 to 3 mol/L, more preferably 0.1 to 1.5 mol/L, even more preferred 0.3 to 1.5 mol/L, particular preferred 0.7 to 1.1 mol/L, more particular preferred 0.1 to 1.0 mol/L, most particular preferred 0.8 to 1.0 mol/L, especially preferred 0.1 to 0.5 mol/L based on the overall volume of the liquid formulation based on the overall volume of the liquid formulation at least one pharmaceutically acceptable alkaline earth metal salt.

In another embodiment the liquid pharmaceutical formulation, preferably being essentially free of water comprises
a) at least one easily degradable active pharmaceutical ingredient of the group consisting of Bendamustine, Chlorambucil, Melphalan, Melflufen, preferably Bendamustine,
b) propylene glycol, 1,3-butanediol, polyethylene glycol, such as PEG 400 and/or PEG 300, preferably PEG 400 and/or propylene glycol.
c) at least calcium chloride or magnesium chloride, preferably calcium chloride.

In a further embodiment the liquid pharmaceutical formulation, preferably being essentially free of water comprises
a) 1 to 200 mg/g, preferably 5 to 150 mg/g, more preferably 10 to 100 mg/g, most preferably 20 to 40 mg/g based on the overall weight of the formulation. of at least one easily degradable active pharmaceutical ingredient of the group consisting of Bendamustine, Chlorambucil, Melphalan, Melflufen, preferably Bendamustine,
b) propylene glycol, 1,3-butanediol, polyethylene glycol, such as PEG 400 and/or PEG 300, preferably PEG 400 and/or propylene glycol and
c) 0.1 to 3 mol/L, more preferably 0.1 to 1.5 mol/L, even more preferred 0.3 to 1.5 mol/L, particular preferred 0.7 to 1.1 mol/L, more particular preferred 0.1 to 1.0 mol/L, most particular preferred 0.8 to 1.0 mol/L, especially preferred 0.1 to 0.5 mol/L based on the overall volume of the liquid formulation of at least calcium chloride or magnesium chloride, preferably calcium chloride.

In another embodiment the liquid pharmaceutical formulation, preferably being essentially free of water comprises
a) at least one active pharmaceutical ingredient of the group consisting of Bendamustine, Melphalan, Melflufen, Chlorambucil, and Uramustine.
b) polyethylene glycol, such as PEG 400 and/or PEG 300, propylene glycol, 1,3-butanediol, preferably polyethylene glycol, propylene glycol or mixtures thereof and
c) at least calcium chloride or magnesium chloride, preferably calcium chloride.

In a further embodiment the liquid pharmaceutical formulation, preferably being essentially free of water comprises
a) 1 to 200 mg/g, preferably 5 to 150 mg/g, more preferably 10 to 100 mg/g, most preferably 20 to 40 mg/g based on the overall weight of the formulation. of at least one active pharmaceutical ingredient of the group consisting of Bendamustine, Melphalan, Melflufen, Chlorambucil, and Uramustine, preferably Bendamustine,
b) propylene glycol, 1,3-butanediol, polyethylene glycol, such as PEG 400 and/or PEG 300, preferably PEG 400 and/or propylene glycol and
c) 0.1 to 3 mol/L, more preferably 0.1 to 1.5 mol/L, even more preferred 0.3 to 1.5 mol/L, particular preferred 0.7 to 1.1 mol/L, more particular preferred 0.1 to 1.0 mol/L, most particular preferred 0.8 to 1.0 mol/L, especially preferred 0.1 to 0.5 mol/L based on the overall volume of the liquid formulation of at least calcium chloride or magnesium chloride, preferably calcium chloride.

In a further embodiment the liquid pharmaceutical formulation, preferably being essentially free of water comprises
a) at least one easily degradable active pharmaceutical ingredient, wherein the degradable active pharmaceutical ingredient is a compound according to formula (II)

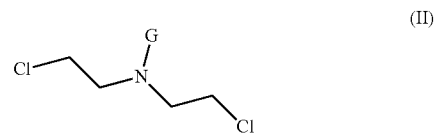

wherein
G is Ar or HetAr
Ar or HetAr is optionally substituted with 1 to 5, preferably 1 to 4, more preferably 1 to 3, particularly preferred 1 to 2, most preferably 1 substituent,
b) propylene glycol, 1,3-butanediol, polyethylene glycol, such as PEG 400 and/or PEG 300, preferably PEG 400 and/or propylene glycol and
c) at least calcium chloride or magnesium chloride, preferably calcium chloride.

Moreover the present invention is directed to the use of the liquid pharmaceutical formulation as defined above, for use in medicine.

The inventive liquid pharmaceutical formulation may be combined with a physiologically acceptable aqueous solution prior to application to the patient. For example the liquid pharmaceutical formulation may be combined with suitable amount of isotonic sodium chloride solution. Preferably the concentration of the isotonic sodium chloride solution comprises 9 mg/L sodium chloride and preferably exhibits a pH value of 4.5 to 7.0.

The present invention further comprises a formulation comprising a) the inventive liquid pharmaceutical formulation, as described above and b) a physiologically acceptable aqueous solution, as well as its use in medicine.

Furthermore, the present invention is directed to the use of the liquid pharmaceutical formulation as defined above, optionally in the presence of water, for use in the treatment of cancer.

Use of at least one pharmaceutically acceptable alkaline earth metal salt in a liquid pharmaceutical formulation, preferably being essentially free of water comprising
a) at least one easily degradable active pharmaceutical ingredient,
b) at least one pharmaceutically acceptable organic solvent and
c) the at least one pharmaceutically acceptable alkaline earth metal salt, for the stabilization of the at least one easily degradable active pharmaceutical ingredient.

The term "stabilization" in the context of the invention means prevention or reduction of degradation of the easily degradable active pharmaceutical ingredient. Preferably it means maintaining a purity as determined by suitable analytical methods of at least 85%, more preferably of at least 90%, most preferably of at least 95% at the end of the defined shelf life of pharmaceutical preparation, in particular compared with a not stabilized sample. For example, the purity may be determined by high-performance-liquid-chromatography (HPLC), in particular reversed phase high-performance liquid-chromatography (RP-HPLC). Furthermore stabilization means that any visible color change of the preparation caused by degradation is prevented or reduced during product shelf life, in particular in comparison with a not stabilized sample.

EXAMPLES OF THE INVENTION

The invention is further illustrated in the following Examples

Example 1: Determination of Bendamustine Quantity and Purity by Reversed Phase Chromatography (RP-HPLC)

The purity of Bendamustine hydrochloride and quantity was determined as follows using a standard curve:
Column type: C18, 100×4.6 mm, 2.6 µm
Mobile phase: A: Water/ACN/TFA=950/50/1 v/v/v
B: Water/ACN/TFA=50/950/1 v/v/v
Column temperature: 25° C.
Autosampler temperature: 25° C.
Flow rate: 1.2 mL/min
Detection wavelength: 234 nm HPLC Gradient

TABLE 1

HPLC Gradient

| Time [min] | Eluent A | Eluent B |
|---|---|---|
| 0 | 95% | 5% |
| 5.00 | 95% | 5% |
| 9.00 | 80% | 20% |
| 25.00 | 55% | 45% |
| 28.00 | 20% | 80% |
| 30.00 | 20% | 80% |
| 30.01 | 95% | 5% |
| 35.00 | 95% | 5% |

Example 2: Stabilizer Solution Study

The solubility of potential stabilizers to be tested for Bendamustine-HCl liquid formulation was evaluated in polypropylene glycol. The respective chemical was dissolved in water under continuous stirring at 40° C. After complete dissolution the solutions were stored at 2° C.-5° C. over-night before analysis to simulate the worst case.

TABLE 2

Stabilizer solubility study results

| Stabilizer | Target concentration [mol/kg] | Outcome |
|---|---|---|
| $CaCl_2$ | 0.9 | Complete dissolution |
| $CaBr_2$ | 0.9 | Complete dissolution |
| $MgCl_2$ | 0.9 | Complete dissolution |
| Choline-HCl | 1.8 | Complete dissolution |

Example 3: Bendamustine HCl Solubility Study

The solvent systems w/ and w/o potential stabilizers listed in Table 3 were compounded. Bendamustine-HCl drug substance was added. The samples were stirred at room temperature and stored overnight at 2-8° C. The concentration of Bendamustine-HCl in each system was quantified after centrifugation in the supernatant by RP-HPLC (Example 1).

TABLE 3

Formulation variants tested for Bendamustine-HCl solubility.

| Formulation variant | Sample description | Comment | Benda HCl [g] | Solvent [g] | Max. Solubility at 2-8° C. [mg/g] |
|---|---|---|---|---|---|
| 1 | Mix, according to WO 2010/036702 A1:, 90% PEG 400/10% PG (w/w) | benchmark | 0.80 | 9.20 | 69 |
| 2 | PG | solvent negative control | 0.80 | 9.20 | 69 |
| 3 | PG, molecular sieve, filtrated | drying agent | 0.80 | 9.20 | 74 |
| 4 | PG, molecular sieve, permanent contact | drying agent | 0.80 | 9.20 | 72 |
| 5 | PG + $CaCl_2$ | stabilizer | 0.80 | 9.20 | 55 |
| 6 | PG + $CaBr_2$ | stabilizer | 0.80 | 9.20 | 17 |
| 7 | PG + Cholin/HCl | Cl⁻ source, according to U.S. Pat. No. 9,572,797 | 0.80 | 9.20 | 70 |
| 8 | PG + Cholin (70 mM) | Patent control | 0.80 | 9.20 | 80 |

The target concentration for Bendamustine-HCl was 80 mg/g. The detected concentrations in the specific formulations after storage over-night at 2-8° C. and subsequent centrifugation are determined by means of RP-HPLC using a standard curve.

Example 4: Bendamustine HCl Stability Study 1

Bendamustin containing compositions were prepared by dissolving Bendamustine-HCl to a concentration of 25 mg/g in one of the formulations #1 to #10 as listed below in Table 4. Samples were stored at 25° C. and 40° C. for 60 days. Content and purity was determined at T=0 and at further time points.

TABLE 4

Formulation variants tested for Bendamustine-HCl stability:

| Formulation variant | Sample description | comment | purity after 60 d at 25° C. | purity after 60 d at 40° C. |
|---|---|---|---|---|
| 1 | Mix, according to WO 2010/036702 A1:, 90% PEG 400/10% PG (w/w) | benchmark | 94.1% | 85.9% |
| 2 | PG | solvent negative control | 4.3% | 1.1% |
| 3 | PG, molecular sieve, filtrated | drying agent | 94.3% | 1.1% |
| 4 | PG, molecular sieve, permanent contact | drying agent | 84.5% | 59.1% |
| 5 | PG + 0.9 mol/kg $CaCl_2$ | drying agent | 98.6% | 94.7% |
| 6 | PG + 0.9 mol/kg $CaBr_2$ | drying agent | 73.6% | 25.2% |
| 7 | PG + 1.8 mol/kg Cholin-HCl | Cl— source | 6.5% | 1.4% |
| 8 | PG + 70 mmol/kg Cholin-HCl | according to U.S. Pat. No. 9,572,797 | 6.0% | 1.6% |
| 9 | PG + 0.9 mol/kg $MgCl_2$ | drying agent | 97.4% | 89.7% |
| 10 | Mix, according to: WO2011/094565 w/ thiogylcerol, 90% PEG 400/10% PG/0.5% monothioglycerol (w/w) | Benchmark, market product | 97.7% | 88.1% |

Purity of Bendamustine-HCl was assessed by evaluating relative main peak areas in RP-HPLC chromatograms. For detailed results see FIG. 2 to FIG. 5.

Formulation variant 5 (PG+0.9 mol/kg $CaCl_2$) showed highest stability of Bendamustine-HCl after 60 days of storage at 25° C. as well as at 40° C., respectively. Specifically, the purity in this formulation variant 5 at the end of the study was determined as 98.6% at 25° C. and 94.7% at 40° C. Formulations 1, 9, and 10 also showed respectable results with 85.9% (variant 1), 89.7% (variant 9), and 88.1% (variant 10) purity at 40° C. Variant 3 (PG+molecular sieve filtered) showed good results at 25° C. with 94.3% purity at the end of the study but then rather bad results at 40° C. with nearly complete degradation during storage (1.1% main peak area). The purity values determined for variant 4 (PG+molecular sieve) showed high fluctuations and were inconsistent which may be due to the rather undefined composition of the formulation containing "a few" sieve pellets per vial.

Example 5: Visual Appearance of Bendamustine HCl Preparations

Figure 6:
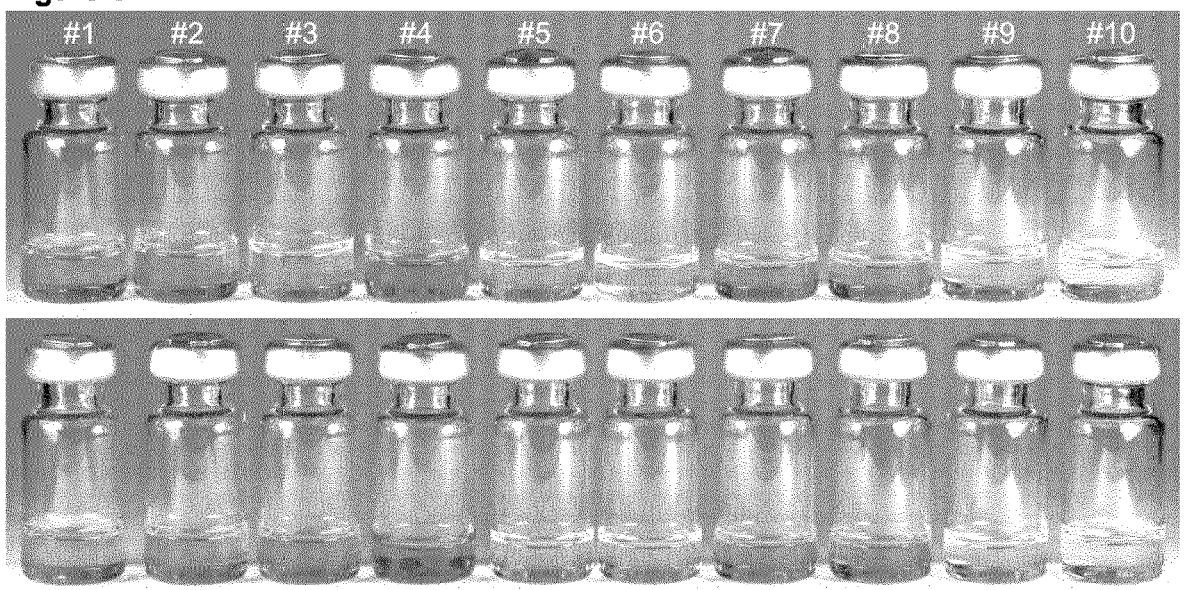
FIG. 6 depicts Photographs of the Bendamustine-HCl stability samples taken after the end of the stability study. Top: stored at 25° C.; Bottom: stored at 40° C.

Due to changes of visual appearance of the samples further underling the RP-HPLC results, macro photographs of vials were taken after the end of the stability study. FIG. 6 shows two photographs comparing all variants.

Again, the superiority of formulation variant 5 (PG+0.9 mol/kg $CaCl_2$) over all other variants is apparent as no color change at all could be detected. All other variants show at least a slight yellow tint (formulation variants 6, 9, and 10) which may be interpreted as some kind of degradation. Interestingly, formulation variants 1 and 10 (benchmark formulation w/and w/o monothioglycerol) also show a rather strong yellow tint, whereby it seems more pronounced in the formulation without monothioglycerol (formulation variant 1).

Example 6: Bendamustine HCl Stability Study 2: Comparative Examples

The following Bendamustine containing compositions (25 mg Bendamustine/HCl in 4 g solution) were prepared, filled into type 1 glass vials. The closed vials were stored at defined temperatures (2-8° C., 25° C. and 40° C.) as shown in the table below.

At defined time point (4 weeks) samples were taken and analyzed be mans of the RP-HPLC method described in Example 1.

TABLE 5

Stability data for 2-8° C., 25° C. and 40° C.

| | Purity after T = 4 weeks [%][1] | | |
|---|---|---|---|
| Solvent composition | 2-8° C. | 25° C. | 40° C. |
| $ZnCl_2$ 0.9 mol/kg in PG | 96.5 | 40.9 | 3.3 |
| $ZnCl_2$ 0.45 mol/kg in PG | 96.4 | 41.3 | 3.2 |
| KAc 0.9 mol/kg in PG | 59.4 | 0.9 | 0.3 |
| $ZnCl_2$ 0.224 mol/kg in PEG400/PG 90/10 | 99.5[2] | 96.4[2] | 84.4[2] |

[1]Bendamustin API: 99.5% purity
[2]Purity after T = 3 weeks [%]

Conclusion: The salts $ZnCl_2$ and KAc, both not belonging to the class of alkaline earth metal salts, are soluble in organic solvents but show no significant stabilizing effect on Bendamustine neither in the propylene glycol nor in the PEG400/PG solvent mixture.

Compared to the degradation rate of Bendamustine in PEG400/PG without addition of mineral salt (see example 8, the degradation of Bendamustine in the PEG400/PG solvent mixture is even more pronounced in presence of co-dissolved $ZnCl_2$.

Example 7: Stability Study of Other Active Pharmaceutical Ingredients

In example 2 it was shown that calcium chloride in propylene glycol had a stabilizing effect on Bendamustine-HCl. To further investigate this phenomenon, other pharmaceutically active molecules with different degradation mechanisms were tested for stability in a 4 weeks short term stability experiment at 40° C. To serve as a direct reference, Bendamustine-HCl was also included in the study. To differentiate between the stabilizing effects, if any, between calcium and chloride all experiments were run in parallel with addition of choline-chloride in the same molar amount in respect to chloride to demonstrate that the stabilizing effect—if any—is attributed to calcium not chloride.

The following compositions were prepared, filled into type 1 glass vials, closed with a rubber stopper and crimp caped. The closed vials were stored at a temperature of 40° C.

TABLE 6

Substances tested in a short term stability study at 40° C.

| API | conc. [mg/g] | formulation | comment |
|---|---|---|---|
| Bendamustine | 25 | $CaCl_2$ 99.9 mg \| PG ad 1000 mg | to confirm previous results |
| Bendamustine | 25 | Choline/HCl 251.3 mg \| PG ad 1000 mg | Cl-source |
| Carmustine | 35 | $CaCl_2$ 99.9 mg \| PG ad 1000 mg | API with untypical N-mustard structure (β-chloro-nitrosourea) |
| Carmustine | 35 | Choline/HCl 251.3 mg \| PG ad 1000 mg | Cl-source |

TABLE 6-continued

Substances tested in a short term stability study at 40° C.

| API | conc. [mg/g] | formulation | comment |
|---|---|---|---|
| Azacytidine | 25 | CaCl$_2$ 99.9 mg \| PG ad 1000 mg | API w/o N-mustard but sensitive to hydrolysis |
| Azacytidine | 25 | Choline/HCl 251.3 mg \| PG ad 1000 mg | Cl-source |
| Melphalan | 5.0 | CaCl$_2$ 99.9 mg \| PG ad 1000 mg | API with arom. N-mustard structure |
| Melphalan | 5.0 | Choline/HCl 251.3 mg \| PG ad 1000 mg | Cl-source |

At defined time points samples were taken and analyzed be mans of the RP-HPLC method described in Example 1.

The following results for content (concentration of API) and purity of the APIs were obtained:

Bendamustine

Figure 7:
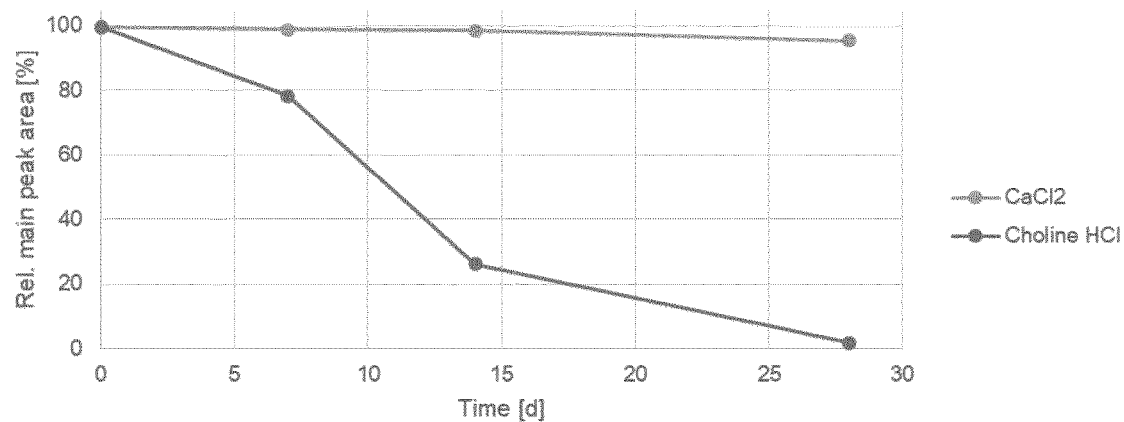
FIG. 7 depicts the Bendamustine purity by RP-HPLC
Figure 8:
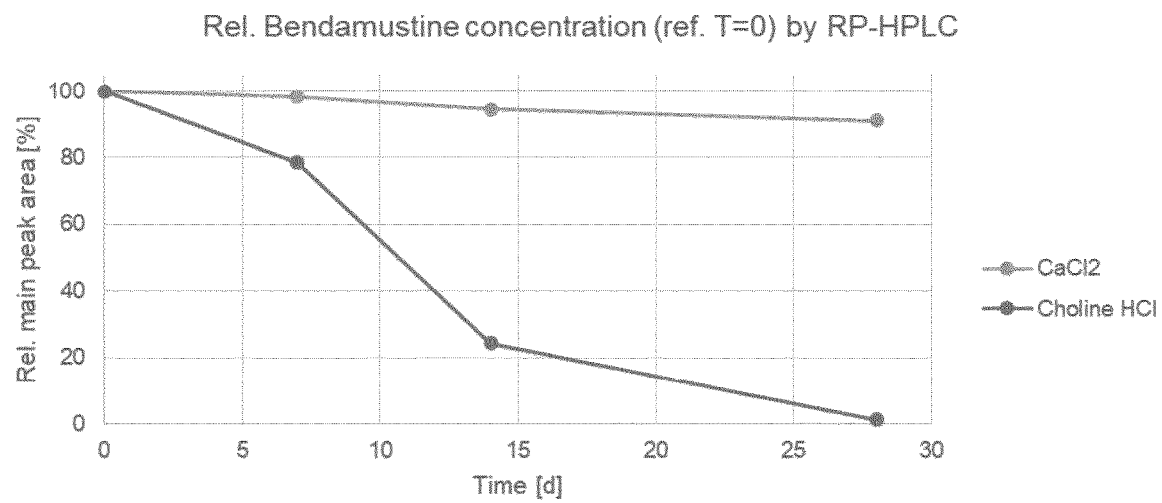
FIG. 8 depicts the Rel. Bendamustine concentration (ref. T=0) by RP-HPLC

The results generated in example 2 could be confirmed. After 4 weeks of storage Bendamustine showed a purity of roughly 95% in the calcium chloride formulation and only about 2% in the Choline-HCl formulation. The concentration dropped accordingly. See FIGS. 7 and 8, as well as tables 7 and 8.

TABLE 7

Purity of Bendamustine at 40° C. as relative main peak area [%] by RP-HPLC.

| | Formulation variant # | |
|---|---|---|
| Time [days] | CaCl$_2$ | Choline HCl |
| 0 | 99.7% | 99.6% |
| 7 | 98.9% | 78.2% |
| 14 | 98.4% | 26.1% |
| 28 | 95.3% | 1.8% |

TABLE 8

Rel. content of Bendamustine at 40° C. determined by RP-HPLC using a calibration curve.

| | Formulation variant | |
|---|---|---|
| Time [days] | CaCl$_2$ | Choline HCl |
| 0 | 100% | 100% |
| 7 | 98.9% | 78.5% |
| 14 | 98.4% | 24.4% |
| 28 | 95.3% | 1.3% |

Azacitidine

Figure 9:
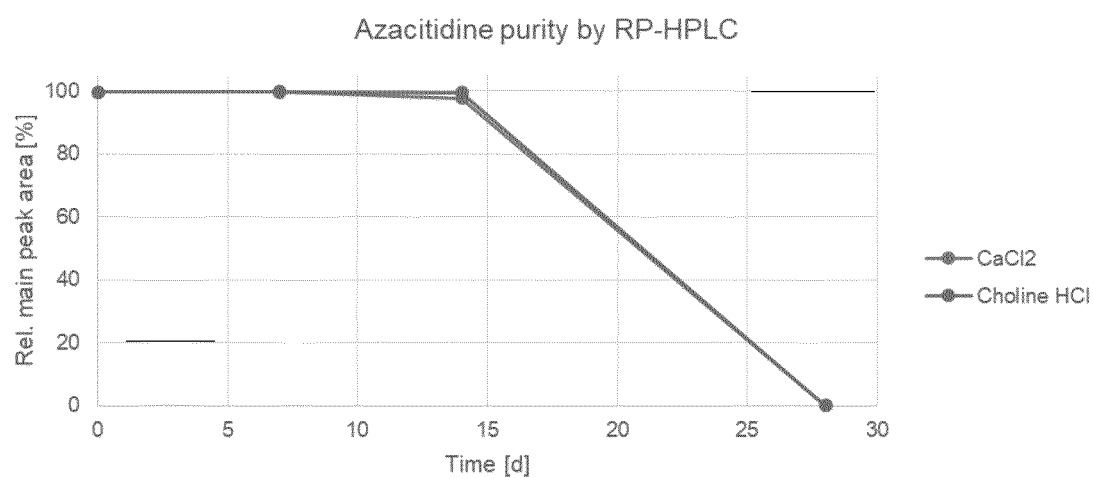
FIG. 9 depicts the Azacitidine purity by RP-HPLC
Figure 10:
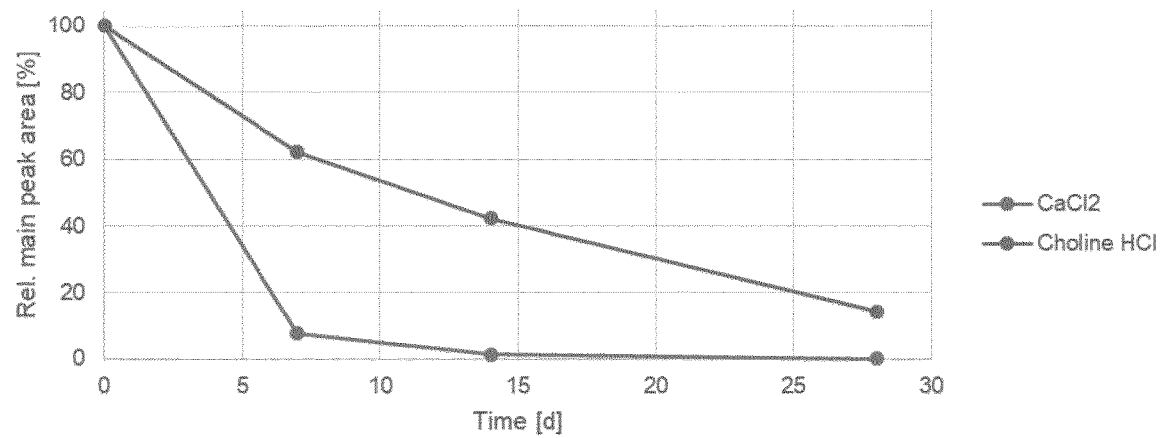
FIG. 10 depicts rel. Azacitidine concentration (ref. T=0) by RP-HPLC

Azacitidine degraded rapidly in both formulations. Calcium chloride showed no stabilizing effect on Azacytidine, as shown in Tables 9, 10 and FIGS. 9, 10.

TABLE 9

Purity of Azacitidine at 40° C. as relative main peak area [%] by RP-HPLC.

| | Formulation variant | |
|---|---|---|
| Time [days] | CaCl$_2$ | Choline HCl |
| 0 | 100% | 100% |
| 7 | 99.8% | 99.8% |
| 14 | 97.7% | 99.5% |
| 28 | 0.0% | 0.0% |

Carmustine

Figure 11:
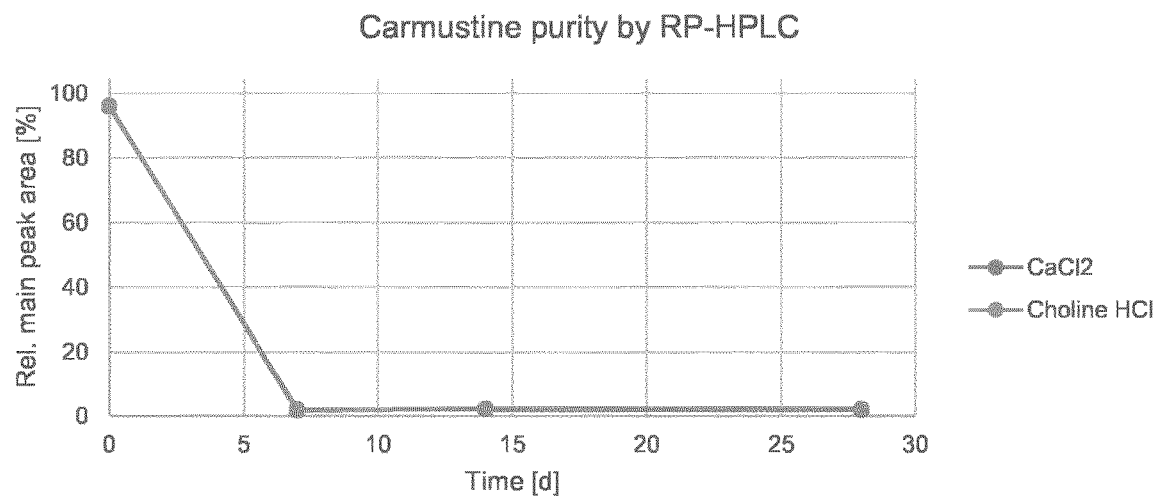
FIG. 11 depicts Carmustine purity by RP-HPLC
Figure 12:
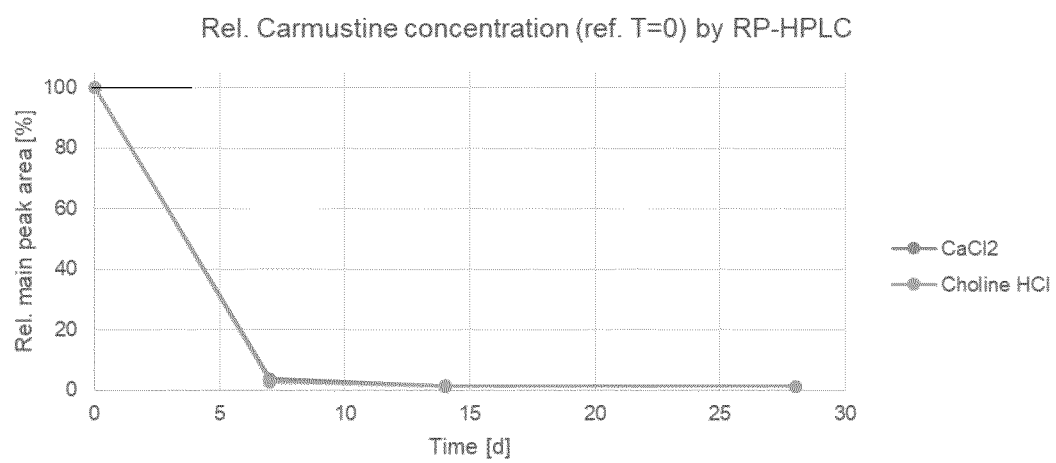
FIG. 12 depicts rel. Carmustine concentration (ref. T=0) by RP-HPLC

Carmustine was completely degraded already after 1 week in both formulations. Calcium chloride showed no stabilizing effect on Carmustine. See FIGS. 11, 12 and tables 10, 11.

TABLE 10

Purity of Carmustine at 40° C. as relative main peak area [%] by RP-HPLC.

| | Formulation variant | |
|---|---|---|
| Time [days] | CaCl$_2$ | Choline HCl |
| 0 | 95.8% | 96.1% |
| 7 | 2.1% | 1.6% |
| 14 | 2.0% | 2.4% |
| 28 | 1.9% | 2.2% |

TABLE 11

Rel. content of Carmustine at 40° C. determined by RP-HPLC using a calibration curve.

| | Formulation variant | |
|---|---|---|
| Time [days] | CaCl$_2$ | Choline HCl |
| 0 | 100% | 100% |
| 7 | 3.6% | 2.6% |
| 14 | 1.3% | 1.4% |
| 28 | 1.3% | 1.2% |

Melphalan

Figure 13:
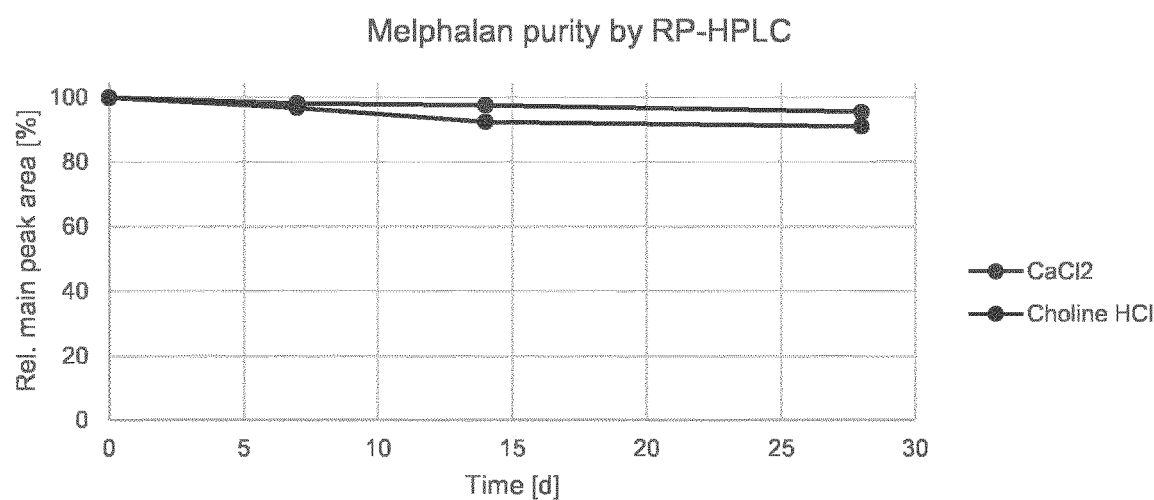
FIG. 13 depicts Melphalan purity by RP-HPLC
Figure 14:
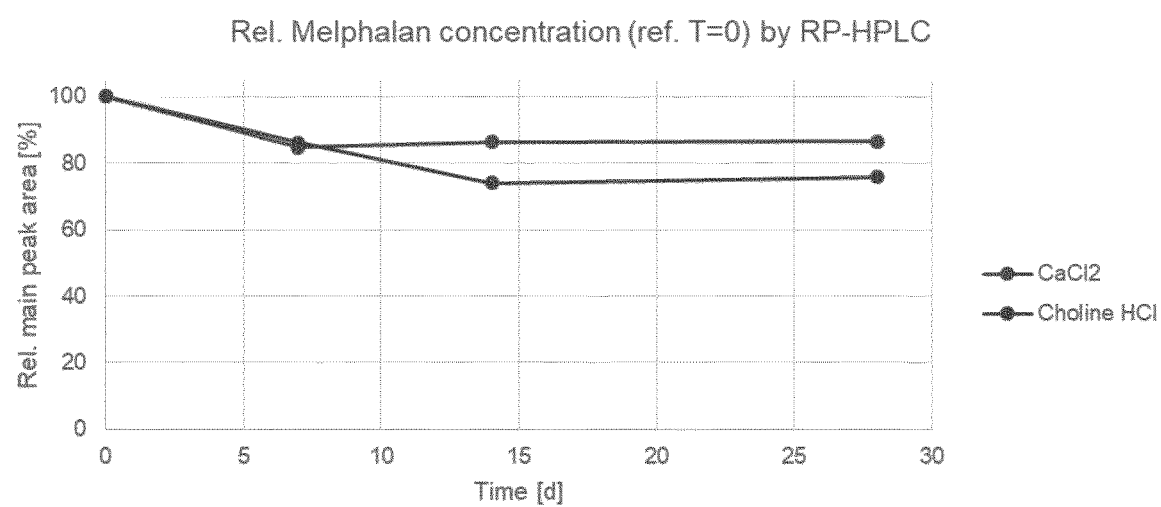
FIG. 14 depicts rel. Melphalan concentration (ref. T=0) by RP-HPLC

Melphalan showed a relatively high stability in the solvent even without stabilizer. However, content and purity of the preparation with calcium chloride was higher than with choline chloride. See FIGS. 13, 14 and tables 12,13.

TABLE 12

Purity of Melphalan at 40° C. as relative main peak area[%] by RP-HPLC.

| | Formulation variant | |
|---|---|---|
| Time [days] | CaCl$_2$ | Choline HCl |
| 0 | 99.8% | 96.7% |
| 7 | 98.1% | 96.6% |
| 14 | 97.4% | 92.4% |
| 28 | 95.4% | 91.0% |

TABLE 13

Rel. content of Melphalan at 40° C. determined
by RP-HPLC using a calibration curve.

| Time [days] | Formulation variant | |
| --- | --- | --- |
| | CaCl$_2$ | Choline HCl |
| 0 | 100% | 100% |
| 7 | 84.6% | 86.1% |
| 14 | 86.2% | 74.0% |
| 28 | 86.5% | 76.9% |

Conclusions

The stabilizing effect of calcium-chloride on the typical N-mustard compound Bendamustine could be reproduced. The stabilizing effect can be clearly attributed to calcium and is not conditioned by chloride as chloride (given as Choline-chloride) has no stabilizing effect (complete degradation within 2 to 4 weeks).

Similar results were seen with Melphalan but due to the per se higher stability of Melphalan compared to Bendamustine the results are less differentiating.

Azacitidine, which is not a N-mustard substance is not stabilized by calcium.

Carmustine, which is not an aromatic nitrogen mustard but a β-chloro-nitrosourea is also not stabilized by calcium.

Example 8: Dose Dependent Stabilization Effect of Calcium Chloride Dissolved in PEG400

The objective of this study was to evaluate the dose depending efficacy of calcium chloride to reduce degradation products during stress storage of Bendamustine-HCl organic liquid formulations. The organic solvent systems PEG400 with a small amount of alcoholic solvents 1,2-propanediol or ethanol (10% w/w) are to be investigated.

The following Bendamustine containing compositions were prepared. All preparations were clearly and colorless soluble and could be sterile filtered through a 0.22 μm PES sterile filter. The preparations were filled into type 1 glass vials and stoppered with nitrogen overlay. The closed vials were stored at 40° C.:

TABLE 14

| # | Bendamus-tine-HCl | Polyethylene glycol 400 | 1,2-Pro-panediol | Ethanol | CaCl$_2$ | 1-Thio-glycerol |
| --- | --- | --- | --- | --- | --- | --- |
| 1 | 0.10 g | 3.44 g | 0.40 g | — | 0.056 g | — |
| 2 | 0.10 g | 3.40 g | 0.40 g | — | 0.099 g | — |
| 3 | 0.10 g | 3.36 g | 0.40 g | — | 0.141 g | — |
| 4 | 0.10 g | 3.64 g | — | 0.20 g | 0.056 g | — |
| 5 | 0.10 g | 3.60 g | — | 0.20 g | 0.099 g | — |
| 6 | 0.10 g | 3.50 g | 0.40 g | — | — | — |
| 7 | 0.10 g | 3.70 g | — | 0.20 g | — | — |
| 8 | 0.10 g | 3.50 g | 0.40 g | — | — | 0.005 g |

At defined time point (4 weeks) samples were taken and analyzed be mans of the RP-HPLC method described in Example 1.

The following results were obtained:

Purity by RP-HPLC

The purity of Bendamustine-HCl was assessed via RP-HPLC and expressed by relative main peak area. Measurements were carried out in duplicate.

TABLE 15

Purity of Bendamustine-HCl at 40° C. as relative
main peak area [%] by RP-HPLC.

| Time [weeks] | Meas. # | Formulation variant # | | | | | | | |
| --- | --- | --- | --- | --- | --- | --- | --- | --- | --- |
| | | 1 | 2 | 3 | 4 | 5 | 6 | 7 | 8 |
| 0 | 1 | 99.8 | 99.8 | 99.8 | 99.8 | 99.8 | 99.8 | 99.7 | 99.9 |
| | 2 | 99.8 | 99.8 | 99.8 | 99.7 | 99.8 | 99.9 | 99.7 | 99.9 |
| 4 | 1 | 95.3 | 96.2 | 96.6 | 94.7 | 95.2 | 93.3 | 91.7 | 93.5 |
| | 2 | 95.3 | 96.1 | 96.6 | 94.5 | 95.4 | 93.2 | 91.6 | 93.5 |
| 8 | 1 | 94.6 | 95.4 | 95.7 | 93.7 | 94.1 | 92.3 | 90.8 | 91.9 |
| | 2 | 94.6 | n.a. | 95.8 | 93.7 | 94.2 | 92.2 | 91.0 | 91.9 |

Figure 15:
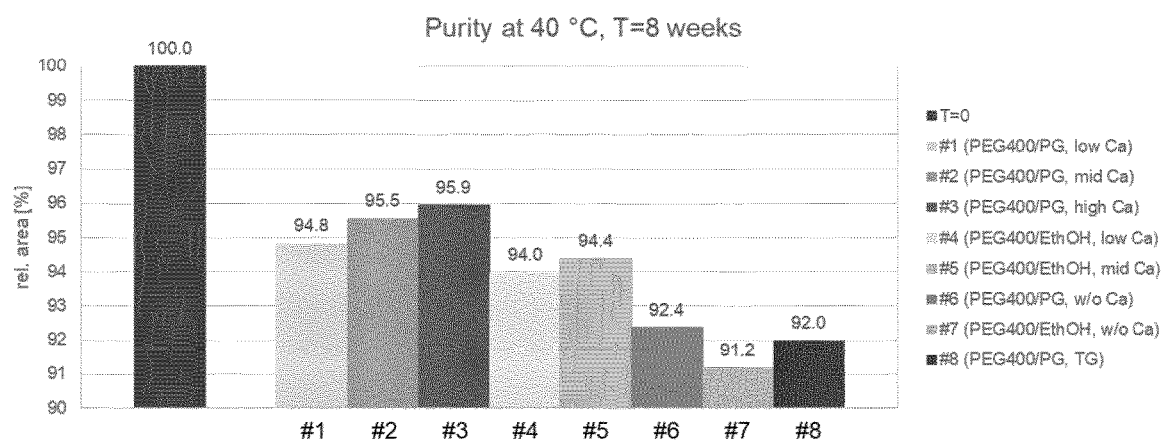
FIG. 15 depicts the purity of Bendamustine-HCl at 40° C. after 8 weeks storage time shown as relative main peak area by RP-HPLC. Displayed are calculated mean values of duplicate measurements, relative to the starting value at T=0.

As displayed in the graph of FIG. 15, the purity was calculated relatively to the value obtained at T=0 (i.e. T=0=100%).

Content by RP-HPLC

The content of Bendamustine-HCl was assessed via RP-HPLC using a 25 mg/g Bendamustine-HCl standard as reference. Standard solutions were freshly prepared for each individual sampling time point. Standard curves were recorded in duplicate at the beginning and at the end of each sequence. Samples were analyzed in duplicate.

TABLE 16

Content [mg/g] of Bendamustine-HCl at 40° C. by RP-HPLC. Target: 25 mg/g

| Time [weeks] | Meas. # | Formulation variant # | | | | | | | |
| --- | --- | --- | --- | --- | --- | --- | --- | --- | --- |
| | | 1 | 2 | 3 | 4 | 5 | 6 | 7 | 8 |
| 0 | 1 | 25.3 | 24.9 | 25.2 | 25.6 | 25.2 | 24.8 | 25.1 | 24.7 |
| | 2 | 25.6 | 25.4 | 25.2 | 25.6 | 24.8 | 25.0 | 25.1 | 24.7 |

TABLE 16-continued

Content [mg/g] of Bendamustine-HCl at 40° C. by RP-HPLC. Target: 25 mg/g

| Time [weeks] | Meas. # | Formulation variant # | | | | | | | |
|---|---|---|---|---|---|---|---|---|---|
| | | 1 | 2 | 3 | 4 | 5 | 6 | 7 | 8 |
| 4 | 1 | 23.4 | 23.7 | 24.1 | 23.3 | 23.5 | 22.1 | 21.8 | 22.6 |
| | 2 | 23.3 | 23.5 | 24.2 | 23.2 | 23.4 | 22.4 | 22.0 | 22.6 |
| 8 | 1 | 22.3 | 23.0 | 23.2 | 22.2 | 22.9 | 21.7 | 21.2 | 21.7 |
| | 2 | 22.9 | n.a. | 23.2 | 22.4 | 22.9 | 21.8 | 21.1 | 21.8 |

Figure 16:
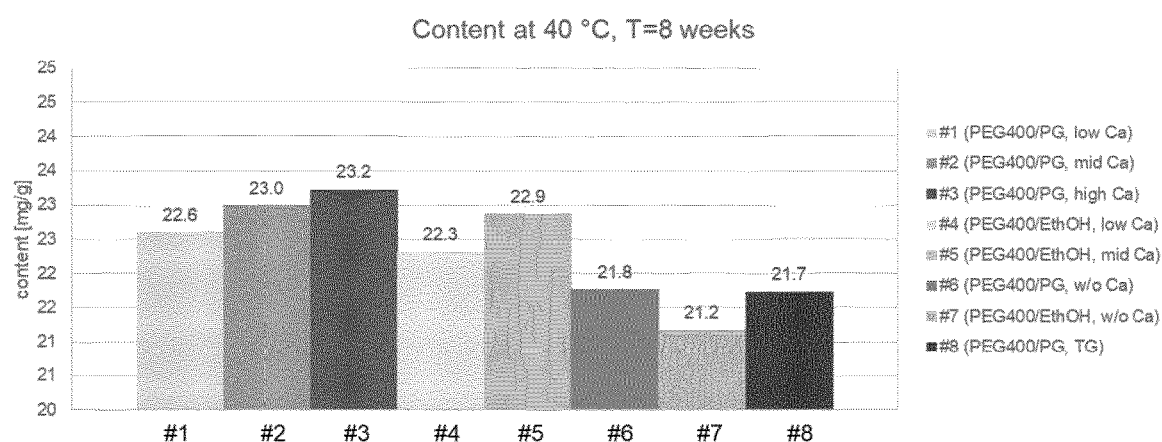
FIG. 16 depicts the content of Bendamustine-HCl at 40° C. after 8 weeks storage time by RP-HPLC. Displayed are calculated mean values of duplicate measurements. Target: 25 mg/g.

In the graph shown in FIG. 16 the content after 8 weeks was calculated relatively to the value obtained at T=0 (i.e. T=0=100%).

Figure 17:
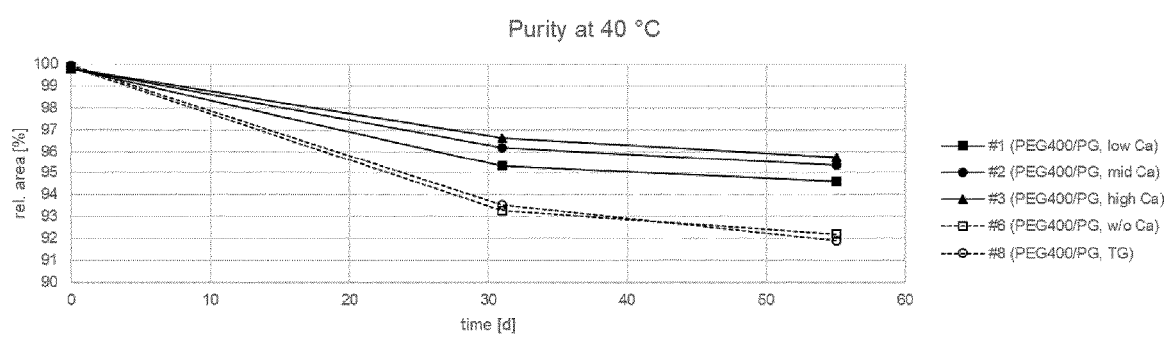
FIG. 17 depicts the purity of Bendamustine-HCl at 40° C. after 8 weeks storage time by RP-HPLC
Figure 18:
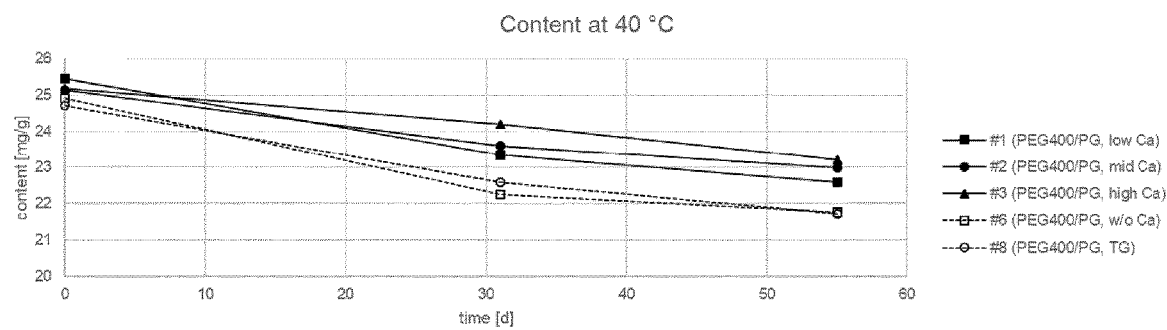
FIG. 18 depicts content of Bendamustine-HCl at 40° C. after 8 weeks storage time by RP-HPLC

In FIGS. 17 and 18, graphs relating purity and content of Bendamustine are shown over storage time (storage temperature 40° C.). Shown are data for the more relevant solvent system PEG 400/PG.

Visual Appearance

Figure 19:
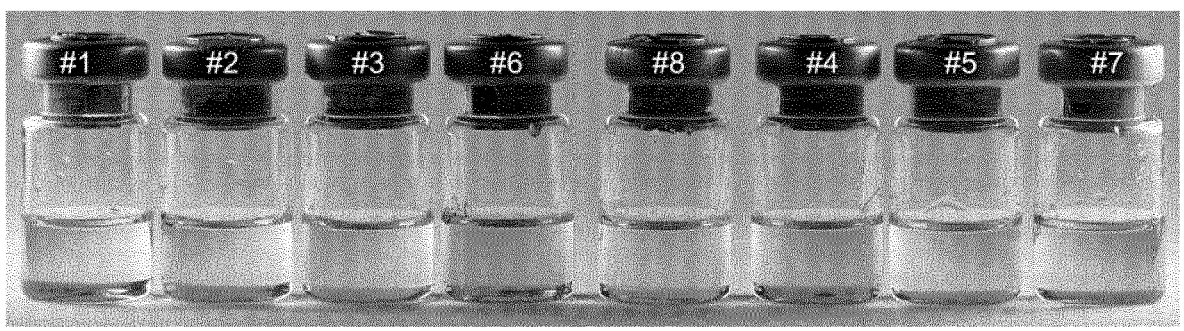
FIG. 19: The visual appearance of the liquid formulations was documented by macro photography. Photographs of representative vials after 8 weeks storage time at 40° C. are displayed.

The visual appearance of the liquid formulations was documented by macro photography. Photographs of representative vials after 8 weeks storage time at 40° C. are displayed (FIG. 19).

Discussion

A clear dose depending stabilizing effect of calcium chloride on Bendamustine could be shown for both solvent mixtures. Content, purity and colorlessness of Bendamustine preparations are better maintained when calcium chloride is added. The solvent system PEG400/PG is superior to PEG400/ethanol, which showed higher degradation rates and coloration. The stabilizer calcium chloride proved to be superior to thioglycerol, which showed a negligible effect only.

Moreover, the invention comprises the following items:
1. A liquid pharmaceutical formulation, being essentially free of water, comprising
   a) at least one easily degradable active pharmaceutical ingredient,
   b) at least one pharmaceutically acceptable organic solvent and
   c) at least one pharmaceutically acceptable alkaline earth metal salt.
2. The liquid pharmaceutical formulation according to item 1, wherein all components of the formulation are completely dissolved resulting in a clear solution.
3. The liquid pharmaceutical formulation according to item 1 or 2, wherein the at least one alkaline earth metal salt is a calcium salt.
4. The liquid pharmaceutical formulation according to any one of items 1 to 3, wherein the at least one alkaline earth metal salt is a magnesium salt.
5. The liquid pharmaceutical formulation according to any one of items 1 to 4, wherein the anion of the at least one alkaline earth metal salt is gluconate, orotate, chloride, bromide, acetate or lactate, preferably chloride.
6. The liquid pharmaceutical formulation according to any one of the items 1 to 5, wherein the at least one pharmaceutically acceptable organic solvent is propylene glycol, 1,3-butanediol, polyethylene glycol such as PEG 400 and/or PEG 300, preferably propylene glycol and/or 1,3-butanediol.
7. The liquid pharmaceutical formulation according to any one of items 1 to 6, wherein the at least one pharmaceutically acceptable alkaline earth metal salt is present in a concentration of 0.1 to 3 mol/L, preferably 0.3 to 1.5 mol/L, more preferably 0.7 to 1.1 mol/L.
8. The liquid pharmaceutical formulation according to any one of items 1 to 7, wherein the easily degradable active pharmaceutical ingredient is sensitive to hydrolysis.
9. The liquid pharmaceutical formulation according to any one of the items 1 to 8, wherein the easily degradable active pharmaceutical ingredient is an alkylating agent.
10. The liquid pharmaceutical formulation according to any one of items 1 to 9, wherein the easily degradable active pharmaceutical ingredient comprises at least one group according to formula (I)

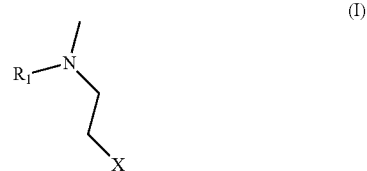

wherein in formula (I),
X is Cl or Br, preferably Cl
$R_1$ is H, —$CH_2CH_2X$ or —NO, preferably H or —$CH_2CH_2X$.
11. The liquid pharmaceutical formulation according to any one of items 1 to 10, wherein the at least one easily degradable active pharmaceutical ingredient is present in a concentration of 1 to 200 mg/g, preferably 5 to 150 mg/g, more preferably 10 to 100 mg/g, most preferably 20 to 40 mg/g based on the overall weight of the formulation.
12. The liquid pharmaceutical formulation according to any one of items 1 to 11, wherein the at least one easily degradable active pharmaceutical ingredient is selected from the group consisting of Carmustine, Lomustine, Nimustine, Bendamustine, Cyclophosphamide, Melphalan, Melflufen, Azacytidine, Chlorambucil, Ifosfamide, Procarbazine, Dacarbazine, Tremozolomide, Mechlorethamine, Thiotepa, Cisplatin, Carboplatin, Oxaliplatin, Busulfan, Treosulfan, and Fosaprepitant, preferably consisting of Bendamustine, Chlorambucil, Carmustine, Lomustin, Cyclophosphamide, Melphalan, Melflufen, Ifosfamide, Mechlorethamine, more preferably consisting of Bendamustine.
13. The liquid pharmaceutical formulation, according to any one of items 1 to 12, optionally in the presence of water, for use in medicine.
14. The liquid pharmaceutical formulation according to any one of items 1 to 13, optionally in the presence of water, for use in the treatment of cancer.
15. Use of at least one pharmaceutically acceptable alkaline earth metal salt in a liquid pharmaceutical formulation, being essentially free of water, comprising a) at least one easily degradable active pharmaceutical ingredient,
b) at least one pharmaceutically acceptable organic solvent and
c) the at least one pharmaceutically acceptable alkaline earth metal salt.

for the stabilization of the at least one easily degradable active pharmaceutical ingredient.

The invention claimed is:

1. A liquid pharmaceutical formulation, having a water content of below 1.0% (w/w) water, comprising
   a) Bendamustine as an active pharmaceutical ingredient;
   b) at least one pharmaceutically acceptable organic solvent comprising propylene glycol, polyethylene glycol 400 (PEG 400) or a mixture of propylene glycol and PEG 400; and
   c) a calcium salt.

2. The liquid pharmaceutical formulation according to claim 1, wherein all components of the formulation are completely dissolved resulting in a clear solution.

3. The liquid pharmaceutical formulation according to claim 1, wherein the anion of the calcium salt is gluconate, chloride, bromide, acetate or lactate.

4. The liquid pharmaceutical formulation according to claim 1, wherein the at least one pharmaceutically acceptable organic solvent is a mixture of propylene glycol and PEG 400.

5. The liquid pharmaceutical formulation according to claim 1, wherein the at least one pharmaceutically acceptable organic solvent comprises at least 80% PEG 400.

6. The liquid pharmaceutical formulation according to claim 1, wherein the calcium salt is present in a concentration of 0.1 to 3 mol/L based on the overall volume of the liquid formulation.

7. The liquid pharmaceutical formulation according to claim 1, wherein the Bendamustine is present in a concentration of 1 to 200 mg/g based on the overall weight of the formulation.

8. The liquid pharmaceutical formulation according to claim 5, wherein the at least one pharmaceutically acceptable organic solvent is a mixture of 5 to 20% propylene glycol and 80 to 95% PEG 400.

9. The liquid pharmaceutical formulation according to claim 5, wherein the at least one pharmaceutically acceptable organic solvent is a mixture of 10% propylene glycol and 90% PEG 400 (w/w).

10. The liquid pharmaceutical formulation according to claim 3, wherein the calcium salt is a chloride.

11. The liquid pharmaceutical formulation according to claim 1, wherein the calcium salt is present in a concentration of 0.1 to 1.5 mol/L based on the overall volume of the liquid formulation.

12. The liquid pharmaceutical formulation according to claim 1, wherein the calcium salt is present in a concentration of 0.3 to 1.5 mol/L, based on the overall volume of the liquid formulation.

13. The liquid pharmaceutical formulation according to claim 1, wherein the calcium salt is present in a concentration of 0.1 to 0.5 mol/L based on the overall volume of the liquid formulation.

14. The liquid pharmaceutical formulation according to claim 1, wherein the Bendamustine is present in a concentration of 5 to 150 mg/g based on the overall weight of the formulation.

15. The liquid pharmaceutical formulation according to claim 1, wherein the Bendamustine is present in a concentration of 10 to 100 mg/g based on the overall weight of the formulation.

16. The liquid pharmaceutical formulation according to claim 1, wherein Bendamustine is present in a concentration of 20 to 40 mg/g based on the overall weight of the formulation.

* * * * *